US00PP20842P2

(12) United States Plant Patent
Tristram

(10) Patent No.: US PP20,842 P2
(45) Date of Patent: Mar. 16, 2010

(54) ***WEIGELA* PLANT NAMED 'WALWEIGEYE'**

(50) Latin Name: *Weigela florida*
Varietal Denomination: WALWEIGEYE

(76) Inventor: David Ralph Tristram, Yapton Lane, Walberton, Arundel, West Sussex (GB) BN18 0AS ( * ) Notice: Subject to any disclaimer, the term of this patent is extended or adjusted under 35 U.S.C. 154(b) by 0 days.

(21) Appl. No.: 12/317,013

(22) Filed: Dec. 16, 2008

Related U.S. Application Data

(60) Provisional application No. 61/009,015, filed on Dec. 20, 2007.

(51) Int. Cl.
*A01H 5/00* (2006.01)

(52) U.S. Cl. ..... Plt./226

(58) Field of Classification Search ..... Plt./226
See application file for complete search history.

*Primary Examiner*—Susan B McCormick Ewoldt

(57) ABSTRACT

A new and distinct cultivar of *Weigela* named 'WALWEIGEYE' a deciduous shrub characterized by upright habit, intense dark-red flower color, and foliage with intense golden-yellow margins and mid-green centers. In combination these traits set 'WALWEIGEYE' apart from all other existing varieties of *Weigela* known to the inventor.

2 Drawing Sheets

Genus: *Weigela.*
Species: *florida.*
Denomination: 'WALWEIGEYE'.

BACKGROUND OF THE INVENTION

This application claims the benefit of priority under 35 U.S.C. 119(e) of U.S. Provisional Application Ser. No. 61/009,015 filed on Dec. 20, 2007, entitled *Weigela* Plant named 'Eyecatcher'. The inventor has selected the denomination 'WALWEIGEYE' for the instant cultivar which will be marketed under the trade designation Eyecatcher.

The present invention relates to a new and distinct cultivar of *WEIGELA* which is grown as an ornamental deciduous shrub for use in garden and landscape. The new cultivar from the family Caprifoliaceae is known botanically as *WEIGELA florida* and will be referred to hereinafter by the cultivar name 'WALWEIGEYE'.

'WALWEIGEYE' was discovered by the inventor in 2004 in Walberton, Sussex, United Kingdom as a naturally occurring branch sport of *Weigela florida* 'Rubidor' (not patented) which the inventor observed in his commercial crop of 'Rubidor'. The inventor selected 'WALWEIGEYE' in Walberton, Sussex, United Kingdom, based on the criteria of flower color and leaf color. The parent of 'WALWEIGEYE' is an individual *Weigela florida* 'Rubidor' which is also the closest comparison variety known to the inventor. 'Rubidor' exhibits yellow foliage and rust-red flower color, whereas 'WALWEIGEYE' is distinguishable by its dark red flower color and its leaf variegation. Moreover, the golden yellow sections of the variegated leaves of 'WALWEIGEYE' are brighter and are a deeper gold than the yellow foliage of 'Rubidor'.

'WALWEIGEYE' is deciduous and exhibits dense upright habit, flowers that are intense dark-red in color, and variegated leaves of intense golden-yellow and mid-green color. After one year's growth, plants of 'WALWEIGEYE' are 40 cm–50 cm in height and 40 cm–50 cm in width. Dimensions at maturity are 1 meter in height and 75 cm in width. 'WALWEIGEYE' is hardy to USDA Zone 4. Pests and disease resistance and susceptibility are similar to the species. Cultural needs include full sun to partial shade, well-draining soil, and regular water. Although 'WALWEIGEYE' can be planted in full sun, care should be taken when choosing a site to avoid areas of strong direct sunlight in order to prevent scorch of leaf margins. In garden and landscape settings, 'WALWEIGEYE' is utilized as a border, screen or background plant.

'WALWEIGEYE' was first asexually propagated in 2005 by the inventor. Asexual propagation was accomplished at the inventor's nursery in Walberton, Sussex, United Kingdom, using softwood cuttings. Since that time, under careful observation, the distinguishing characteristics of 'WALWEIGEYE' have been determined stable, uniform, and reproduce true to type in successive generations of asexual propagation.

SUMMARY OF THE INVENTION

The following traits have been repeatedly observed and represent the distinguishing characteristics of the new *Weigela* cultivar named 'WALWEIGEYE'. These traits in combination distinguish 'WALWEIGEYE' from all other existing varieties of *Weigela florida* known to the inventor. 'WALWEIGEYE' has not been tested under all possible conditions and phenotypic differences may be observed with variations in environmental, climatic, and cultural conditions without however any variance in genotype.

1. 'WALWEIGEYE' is deciduous.
2. The foliage of 'WALWEIGEYE' is variegated intense golden-yellow and green.
3. Each leaf of 'WALWEIGEYE' exhibits a broad intense golden-yellow margin that includes the leaf apex.
4. Each leaf of 'WALWEIGEYE' exhibits a central green patch of mid-green which does not extend to any margin.
5. The flower of 'WALWEIGEYE' is intense dark-red in color.
6. The flowers of 'WALWEIGEYE' bloom late spring and early summer.
7. After one year from a cutting 'WALWEIGEYE' achieves a height of 40 cm–50 cm and a width of 40 cm 50 cm.

8. A three-year-old plant of 'WALWEIGEYE' is approximately 1 meter in height and 75 cm. in width.
9. 'WALWEIGEYE' is hardy to USDA Zone 4.
10. 'WALWEIGEYE' requires protection from strong direct sunlight to avoid scorch of the leaf margins.

BRIEF DESCRIPTION OF THE DRAWINGS

The accompanying color drawings illustrate the overall appearance of the new *Weigela florida* cultivar named 'WALWEIGEYE' showing color of foliage and flowers as true as it is reasonably possible to obtain in color reproductions of this type. Color in the drawings may differ from color values cited in the detailed botanical description, which accurately describe the actual color of the new variety named 'WALWEIGEYE'.

The drawing labeled

The drawing labeled

Figure 1:
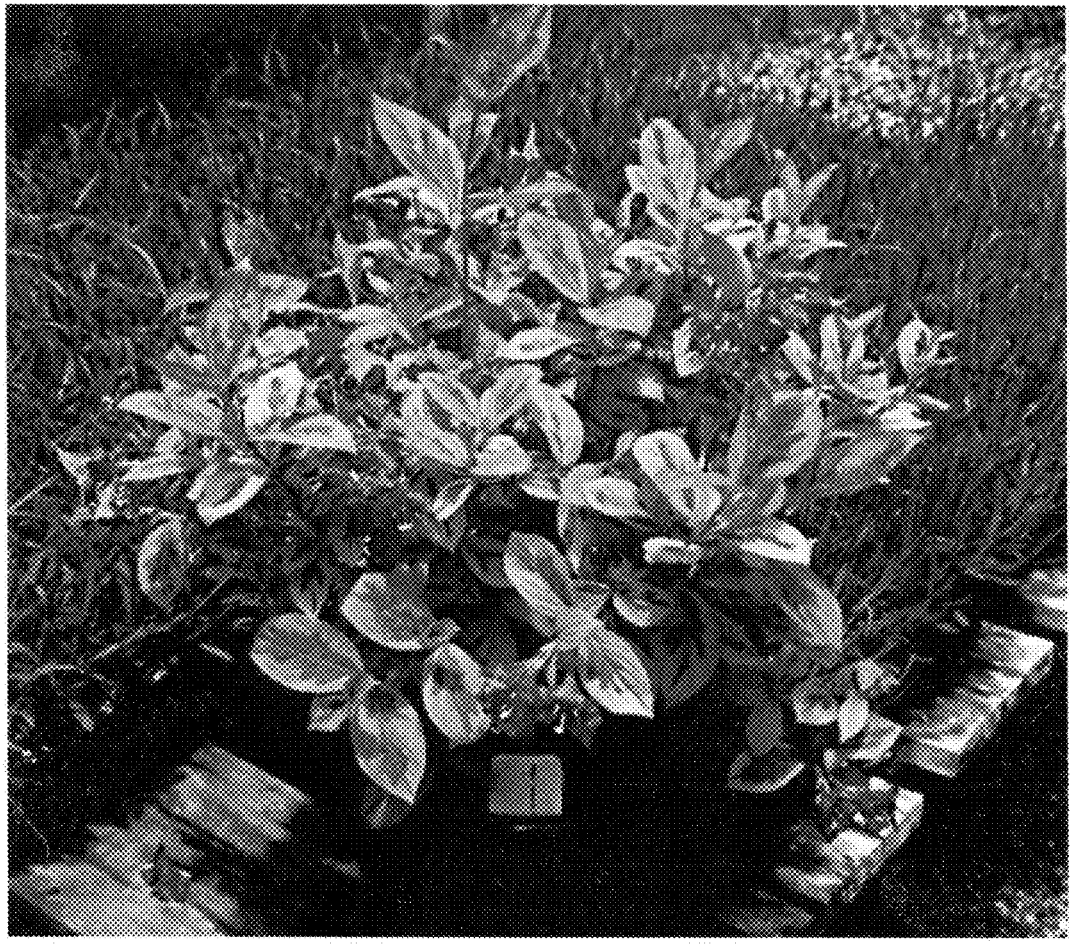
FIG. 1 depicts a single plant of 'WALWEIGEYE' in flower during the month of May. The illustrated plant is two-years-old and planted in a 2-liter container growing out-of doors in Arroyo Grande, Calif.
Figure 2:
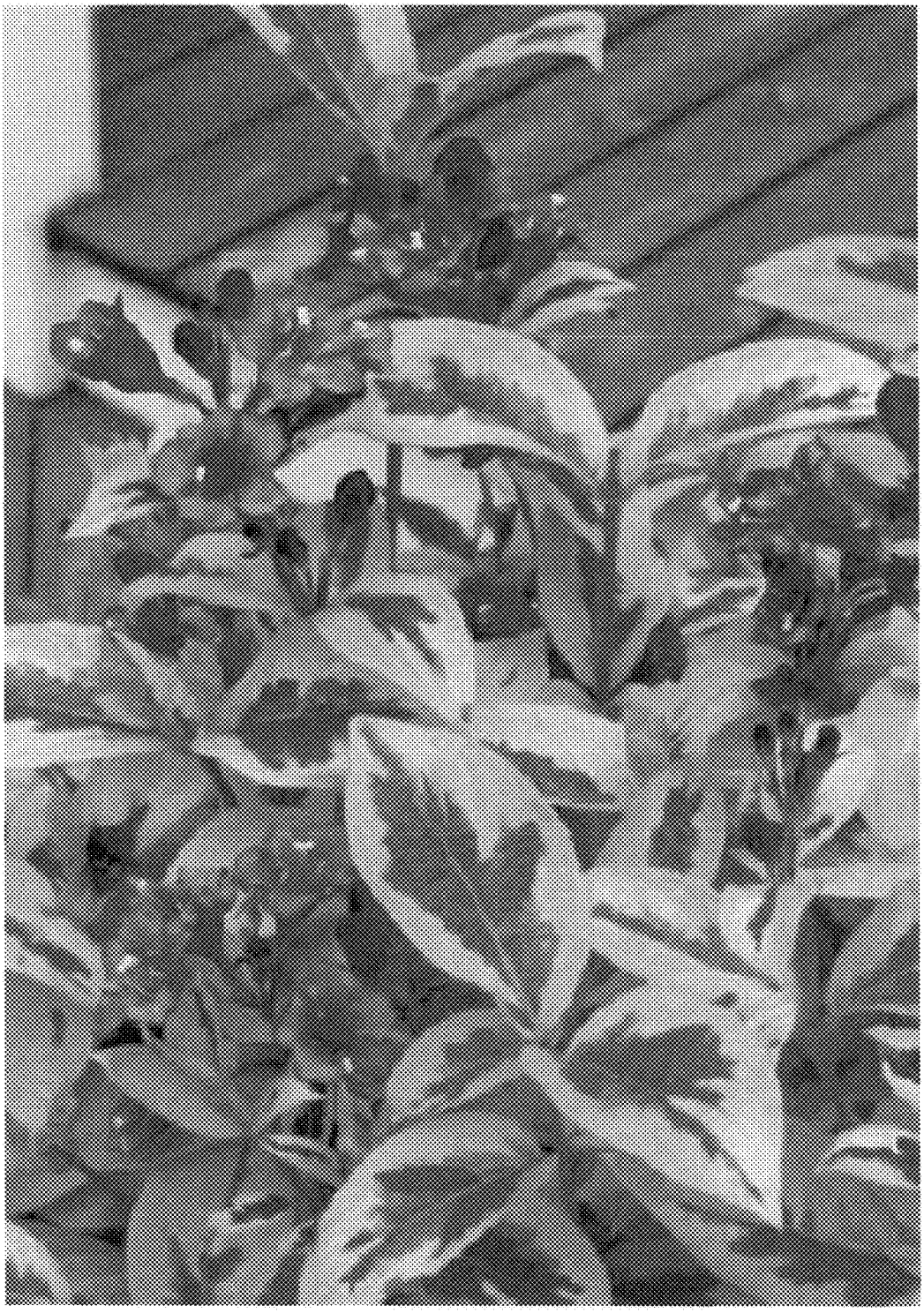
FIG. 2 depicts a close-up view of foliage and flowers of 'WALWEIGEYE'.

Both drawings were made using conventional techniques and although flower and foliage color may appear different from the actual color due to light reflectance, they are as accurate as possible by conventional photography.

BOTANICAL DESCRIPTION OF THE PLANT

The following is a detailed botanical description of the new *Weigela* cultivar named 'WALWEIGEYE'. Observations, measurements, values and comparisons were collected in Arroyo Grande, Calif. from two-year-old plants in 2-liter containers that were grown out-of-doors. Color determinations are made in accordance with The Royal Horticultural Society Colour Chart of 2001 from London England, except where general color terms of ordinary dictionary significance are used. The growing requirements of the new variety are similar to the species.

Botanical classification: *WEIGELA florida* 'WALWEIGEYE'.
Family: Caprifoliaceae.
Genus: *WEIGELA.*
Species: *florida.*
Denomination: 'WALWEIGEYE'.
Common name: *Weigela.*
Parentage: *WEIGELA florida* 'WALWEIGEYE' was discovered as a branch sport growing in a commercial crop of the following parent:
  *Parent.*—An individual *Weigela florida* 'Rubidor' (not patented).
Propagation method: Softwood cuttings.
Rooting habit: Fibrous.
Time to develop roots (range): Approximately 30–45 days are required to develop roots from an initial cutting.
Crop time (average): 6 months are required to achieve a finished 1-liter container from a rooted cutting.
Plant habit: Upright.
Commercial classification: Ornamental shrub.
Use: For garden and landscape as a screen, border, or background plant.
Vigor: Moderate.
Plant dimensions (12 months): 40 cm.–50 cm. in height and 40 cm.–50 cm. in width.
Plant dimensions (3 years): 1 meter in height and 75 cm. in width.
Hardiness: USDA Zone 4.
Cultural requirements: Full sun to partial shade, regular water, and well-draining soil.
Pests and disease: Typical to other *Weigela.*
Pest and disease resistance: None known to the inventor.
Special considerations: Protect from strong direct sunlight to prevent scorch of leaf margin. To maintain vigor prune annually after flowers are spent.
Stem:
  *Stem color.*—164A.
  *Stem shape.*—Sub-cylindrical.
  *Stem width.*—3 mm.
  *Stem length* (*range*).—10–20 cm.
  *Internode* (*range*).—1 cm. to 1.25 cm.
  *Stem surface.*—Scurfy.
Foliage:
  *Type.*—Winter deciduous.
  *Leaf arrangement.*—Opposite.
  *Leaf division.*—Simple.
  *Leaf shape.*—Oval.
  *Leaf length* (*average*).—7 cm.
  *Leaf width* (*average*).—3 cm.
  *Leaf apex* (*range*).—Acute to acuminate.
  *Leaf base* (*range*).—Rounded to aequilateral.
  *Leaf color* (*adaxial surface*).—162A, 153D and 146B are all individually present.
  *Leaf color* (*abaxial surface*).—161A, 153D and 147B are all individually present.
  *Leaf venation pattern.*—Pinnate.
  *Vein color* (*abaxial and adaxial surfaces*).—153D.
  *Leaf margin.*—Crenulate.
  *Leaf surface* (*adaxial*).—Puberulent.
  *Leaf surface* (*abaxial*).—Villous.
  *Leaf attachment.*—Petiolate.
  *Petiole shape.*—Flattened sub-cylindrical.
  *Petiole length* (*range*).—3–6 mm. in length and 1 mm. in width.
  *Petiole surface.*—Villous.
  *Petiole color.*—153B.
  *Stipules.*—None observed.
  *Leaf fragrance.*—None observed.
Flower:
  *Inflorescence type.*—Corymb.
  *Corolla shape.*—Funnel.
  *Corolla color* (*ventral surface*).—60B and 59D are both present.
  *Corolla color* (*dorsal surface*).—59B and 59D are both present.
  *Corolla diameter.*—2.5 cm.
  *Corolla depth.*—3 cm.
  *Lobes.*—5 in number.
  *Lobe color* (*abaxial and adaxial surfaces*).—59D.
  *Lobe dimensions.*—1 cm. in width and 0.50 cm. in length.
  *Fused or unfused.*—Partially fused.
  *Lobe apex.*—Rounded to obtuse.
  *Lobe surface* (*abaxial and adaxial*).—Glabrous.
  *Lobe margin.*—Entire.
  *Lobe arrangement in bud.*—Imbricate.
  *Bud dimensions* (*average*).—2 cm. in length and 0.75 cm. in width.
  *Bud apex* (*range*).—Acute to obtuse.
  *Bud shape.*—Ovoid.
  *Bud color.*—59B.
  *Bud surface.*—Puberulent.

*Flowering season.*—Late spring and early summer.
*Aspect.*—Facing outward and upward.
*Flower quantity* (*average, approximately*).—200 per 3-year-old plant.
*Peduncle dimensions* (*average*).—1.25 cm. in length and 2 mm. in width.
*Peduncle shape.*—Cylindrical.
*Peduncle surface.*—Puberulent.
*Peduncle color.*—59D and 146C.
*Calyx shape.*—Campanulate.
*Calyx color.*—59D.
*Calyx surface.*—Villous.
*Calyx dimensions.*—0.50 cm. in height and 0.40 cm. in width.
*Number of sepals.*—5 in number.
*Fused or unfused.*—Unfused.
*Sepal apex.*—Acute.
*Sepal margins.*—Entire.
*Sepal color* (*adaxial and abaxial surfaces*).—59D.
*Flower fragrance.*—None observed.

Reproductive organs:
*Stamens.*—5 in number.
*Stamen length* (*average*).—2 cm.
*Stamen color.*—59D and 11D.
*Anther length* (*average*).—3 mm.
*Anther color.*—161A.
*Pollen color.*—162A.
*Pollen quantity.*—Moderate.
*Pistil.*—One in number.
*Pistil length* (*average*).—3 cm.
*Pistil color.*—11D.
*Stigma color.*—155A.
*Stigma length.*—<1 mm. in height; 3 mm. in width.
*Style.*—Unbranched.
*Ovary position.*—Inferior.
*Ovary shape.*—Ovoid.
*Ovary dimensions.*—3 mm. in height and 2 mm. in diameter.
*Ovary color.*—151A.

Seed: No seed has been observed to date.

The invention claimed is:

1. A new and distinct variety of *Weigela* plant named 'WALWEIGEYE' as illustrated and described herein.

* * * * *